United States Patent [19]

Brewer et al.

[11] Patent Number: 4,636,508
[45] Date of Patent: Jan. 13, 1987

[54] 5-PYRIMIDINECARBOXYAMIDES AND TREATMENT OF LEUKEMIA THEREWITH

[75] Inventors: Arthur D. Brewer, Puslinch, Canada; John A. Minatelli, Watertown, Conn.

[73] Assignees: Uniroyal Chemical Company, Inc., Middlebury, Conn.; Uniroyal Ltd., Don Mills, Canada

[21] Appl. No.: 725,736

[22] Filed: Apr. 22, 1985

[51] Int. Cl.$^4$ ............... A61K 31/515; A61K 31/505; C07D 239/52; C07D 239/60
[52] U.S. Cl. .................................... 514/274; 514/49; 514/50; 514/269; 514/908; 536/23; 544/301; 544/319
[58] Field of Search ............... 544/301, 319; 514/269, 514/274, 908, 49, 50; 536/23

[56] References Cited

U.S. PATENT DOCUMENTS

| | | | |
|---|---|---|---|
| 3,961,061 | 6/1976 | Krämer et al. | 544/301 |
| 4,229,454 | 10/1980 | Beriger | 544/301 |
| 4,349,552 | 9/1982 | Takaya et al. | 514/274 |
| 4,399,280 | 8/1983 | de Sousa et al. | 544/301 |

FOREIGN PATENT DOCUMENTS

| | | |
|---|---|---|
| 39-1445 | 2/1964 | Japan . |
| 56-25166 | 3/1981 | Japan ................... 514/274 |
| 58-43960 | 3/1983 | Japan ................... 514/274 |

OTHER PUBLICATIONS

Brewer et al., *Biochemical Pharmacology*, vol. 34, No. 11, pp. 2047–2050, 1985.

Primary Examiner—Mark L. Berch
Assistant Examiner—Stephen M. Kapner
Attorney, Agent, or Firm—Marc S. Gross; John A. Shedden

[57] ABSTRACT

Novel 5-pyrimidinecarboxamides useful for regressing or inhibiting the growth of leukemia and tumors. The compounds have the formula:

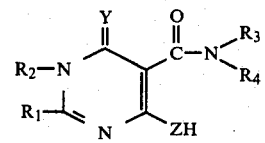

wherein $R_1$ is hydrogen or an alkoxy group having from one to four carbon atoms;

$R_2$ is hydrogen; alkyl, aryl, aralkyl, allyl, aralkenyl or aralkynyl, the alkyl, alkenyl or alkynyl moieties of which have from one to six carbon atoms, or a carbohydrate residue;

$R_3$ is hydrogen, $C_1$–$C_4$ alkyl or aryl;

$R_4$ is phenyl, naphthyl, benzyl, naphthylmethyl, thienyl, thienylmethyl or pyridyl; or phenyl, naphthyl, benzyl, naphthylmethyl, thienyl, thienylmethyl or pyridyl substituted with one or more of the following groups: hydroxy; halo; alkyl, alkoxy, alkylthio, haloalkyl or haloalkoxy having from one to four carbon atoms; carboxy; alkoxycarbonyl having from two to five carbon atoms; nitro; cyano; aryl; aryloxy; arylthio; benzyl; benzyloxy; naphthylmethyl; naphthylmethyloxy; thienyl; or thienylmethyl; and Y and Z are each independently oxygen, sulfur or selenium; and the pharmacologically acceptable addition salts thereof.

6 Claims, No Drawings

5-PYRIMIDINECARBOXYAMIDES AND TREATMENT OF LEUKEMIA THEREWITH

TECHNICAL FIELD

This invention relates to new 5-pyrimidinecarboxamides, and the pharmacologically acceptable addition salts and nucleosides thereof. More particularly, the invention relates to new 5-pyrimidinecarboxamide derivatives which have anti-leukemia and anti-tumor activity, to pharmaceutical compositions containing such derivatives as the therapeutically effective constituents thereof and to a method utilizing the same for inducing the regression of leukemia and/or the inhibition of growth of tumors in mammals.

It is among the objects of the present invention to provide a new class of 5-pyrimidinecarboxamides, in particular a new group of 5-pyrimidinecarboxamides and 2-alkoxy-5-pyrimidinecarboxamides, which are useful anti-leukemia and anti-tumor agents, as well as pharmaceutical compositions and therapeutic methods for utilizing the same. Other objects and advantages of the invention will be apparent from the following detailed description of preferred embodiments thereof.

SUMMARY OF THE INVENTION

The novel 5-pyrimidinecarboxamides of the present invention are the 5-pyrimidinecarboxamides and 2-alkoxy-5-pyrimidinecarboxamides derivatives of the formula:

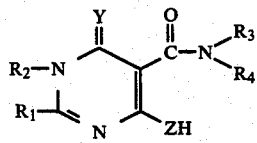

wherein $R_1$ is hydrogen or an alkoxy group having from one to four carbon atoms;

$R_2$ is hydrogen; alkyl, aryl, aralkyl, allyl, aralkenyl or aralkynyl, the alkyl, alkenyl or alkynyl moieties of which have from one to six carbon atoms; or a carbohydrate residue;

$R_3$ is hydrogen, $C_1$-$C_4$ alkyl or aryl;

$R_4$ is phenyl, naphthyl, benzyl, naphthylmethyl, thienyl, thienylmethyl or pyridyl; or phenyl, naphthyl, benzyl, naphthylmethyl, thienyl, thienylmethyl or pyridyl substituted with one or more of the following groups: hydroxy; halo; alkyl, alkoxy, alkylthio, haloalkyl or haloalkoxy having from one to four carbon atoms; carboxy; alkoxycarbonyl having from two to five carbon atoms; nitro; cyano; aryl; aryloxy; arylthio; benzyl; benzyloxy; naphthylmethyl; naphthylmethyloxy; thienyl; or thienylmethyl; and Y and Z may each independently be oxygen, sulfur or selenium; and the pharmacologically acceptable addition salts thereof.

The addition salts may be formed with a variety of pharmacologically acceptable organic and inorganic salt-forming reagents. Useful addition salts may thus be formed by admixture of the organic acid with one equivalent of a base, e.g., an organic amine such as triethylamine or N-methyl glucamine, and inoganic cations such as sodium, potassium or the like. The addition salts of the organic acids of the invention are, in general, crystalline solids which are relatively insoluble in both polar solvents such as water, methanol and ethanol, and non-polar organic solvents such as diethyl ether, benzene, toluene and the like. They are somewhat soluble in aprotic solvents such as dimethylformamide and dimethylsulfoxide.

On the other hand, when $R_2$ is a carbohydrate residue it may be furanosyl (e.g., ribofuranosyl), pyranosyl (e.g., arabinopyranosyl, glucopyranosyl, or galactopyranosyl), their deoxy derivatives, or their aliphatic analogs (e.g., hydroxyalkoxyalkyl or polyhydroxyalkyl groups having from 2 to 12 carbon atoms in each of the alkoxy and alkyl moieties thereof, such as 2-hydroxyethoxymethyl or 2,3-dihydroxypropyl. As used herein, the term "carbohydrate residue" is intended to refer to those cyclic and acyclic groups which form pyrimidine nucleosides or the pseudo nucleosides, e.g., materials including both the cyclic and acyclic groups specified hereinabove.

The 5-carboxyamides of the invention can exist in the form illustrated in the above formula or in any of its tautomeric forms. For ease of understanding, the compounds of the invention will only be illustrated herein in the form shown in the above formula but will be understood to embrace the tautomers thereof, or tautomeric mixtures.

The 5-pyrimidinecarboxamides of the invention may be readily prepared by reacting 4,6-dihydroxypyrimidine or an appropriate 4,6-dihydroxy-2-alkoxypyrimidine with phenylisocyanate or an appropriate substituted phenylisocyanate, in the presence of a solvent or dispersing medium such as dimethylsulfoxide, pyridine, dimethylformamide, N-methylpyrrolidone, dimethylacetamide, sulfolane, tetrahydrothiophene oxide, acetonitrile, or a tertiary amine such as triethylamine. The molar proportions of the pyrimidine to the phenylisocyanate reactant may range from about 2:1 to 1:2, and are preferably from about 1.1:1 to 1:1.1, stoichiometric proportions generally sufficing. The reaction may be carried out at temperatures varying from about 0° to 200° C., usually at from about 24° to 160° C.; in most cases, the reaction proceeds quite well at temperatures of from about 80° to 100° C. Formation of the 5-carboxamides is substantially complete within reaction periods varying from about ½ to 6, and usually from about 2 to 4, hours.

Alternatively, the 5-pyrimidinecarboxamides may be prepared from the corresponding 2-thioxo-5-pyrimidinecarboxamides described in copending application Ser. No. 699,776 filed on Feb. 8, 1985 (5933 KON 1A), by reduction with Raney Nickel.

The 2-alkoxy-5-pyrimidinecarboxamides may also be prepared by reacting an O-alkylpseudourea with an appropriately substituted 2-aroylamino propanedioic acid diester (prepared by reacting a malonic acid diester with an appropriate substituted or unsubstituted aryl isocyanate), e.g., [(phenylamino)carbonyl]propanedioic acid diethyl ester, and separating and recovering the resulting products.

The novel compounds of the invention are cytotoxic agents useful to induce the regression of blood malignancies such as leukemia, as well as to inhibit the growth of solid and non-solid tumors. They may be used alone or in combination with other chemotherapeutic agents active for these purposes. As used herein, the terms "regression" and "inhibition" comprehend arresting or retarding the growth of the malignancy or other manifestation of the disease, as compared with the course of the disease in the absence of treatment.

Administration of the novel 5-carboxamides to mice in amounts ranging from about 12–200 mg./kg., preferably from about 25–100 mg./kg., of body weight has been found effective to induce the regression of leukemia and to inhibit the growth of tumors. The interrelationship of dosages for mammals of other sizes and species is described by Freireich, E. J., et al., Quantitative Comparison of Toxicity of Anti-cancer Agents in Mouse, Rat, Hamster, Dog. Monkey and Man, Cancer Chemotherapy, Reg. 50, No. 4,219–244, May 1966.

The dosage level may, of course, be adjusted to provide optimum therapeutic response. For example, several divided doses may be administered daily, or the dose may be proportionally reduced, as indicated by the exigencies of the therapeutic situation.

The active compounds may suitably be administered parenterally intraperitoneally, intravenously or orally. Solutions or dispersions of the active compounds can be prepared in water, suitably mixed with a surfactant such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. For such uses the form must be sterile and must be fluid to the extent necessary to provide easy syringability. It must be stable under the conditions of manufacture and storage and must be preserved against the contaminating action of microorganisms such as bacteria and fungi.

The carrier can be a solvent or dispersing medium contaning, for example, water, ethanol, a polyol (for example, glycerol, propylene glycol, and liquid polyethylene glycol, or the like), suitable mixtures thereof, and vegetable oils. The proper fluidity can be maintained, for example, by the use of a coating such as lecithin, by the maintenance of the required particle size in the case of a dispersion, and by the use of surfactants. Prevention of the action of microorganisms can be insured by various anti-bacterial and antifungal agents, for example, paraben chlorobutanol, phenol, sorbic acid, thimerosal or the like. In many cases it may be preferable to include isotonic agents, for example sugars or sodium chloride, in the dosage form. Prolonged absorption of the injectable formulations can be brought about by incorporating agents delaying absorption, for example, aluminum monostearate and gelatin, therein.

Sterile injectable solutions are prepared by incorporating the active compound in the appropriate solvent, in admixture with various of the other ingredients enumerated above, as required, followed by filtered sterilization. Generally, dispersions are prepared by incorporating the sterilized active ingredient in a sterile vehicle which contains the dispersing medium and any other required ingredients. When, on the other hand, sterile powders are used to prepare sterile injectable solutions, it is preferred to subject a sterile, filtered solution of the desired ingredients to vacuum drying or freeze-drying, yielding a powder of the active ingredient plus any additional desired ingredients.

As used herein, "pharmaceutically acceptable, substantially nontoxic carrier or excipient" includes solvents, dispersing media, coatings, antibacterial and antifungal agents, isotonic and absorption delaying agents and the like. The use of such media and agents as carriers or excipients for pharmaceutically active substances is well known in the art. Except insofar as any conventional medium or agent is incompatible with the active ingredient or toxic, its use in the therapeutic formulations of the invention is contemplated. Supplementary active ingredients can also be incorporated in the therapeutic compositions.

It may be advantageous to formulate the compositions of the invention in unit dosage forms for ease of administration and uniformity of dosage. A unit dosage form, as used herein, refers to a physically discrete unit suitable for use as a unitary dosage for the mammalian subjects to be treated; each unit contains a predetermined quantity of active material calculated to produce the desired therapeutic effect, in association with the required pharmaceutically acceptable carrier. Specifications for unit dosage forms are dictated by and directly depend on (a) the unique characteristics of the active material and the particular therapeutic effect to be achieved, and (b) the limitations inherent in the art of compounding such an active material for the treatment, of disease in living subjects having a diseased condition, without excessive cytotoxic side effects.

Regression of leukemia and inhibition of tumor growth may be attained, for example, by the use of daily dosing for up to 5 or 10 days, or longer. Multiple dosing, or dosing on any desired periodic basis, may also be utilized. The therapeutically active ingredient is thus administered in amounts sufficient to aid regression and inhibition of further growth of the leukemia or tumor, in the absence of excessive deleterious side effects of a cytotoxic nature.

BEST MODE FOR CARRYING OUT THE INVENTION

Preferred among the 5-carboxamides hereof are 3,4 dihydro-4-hydroxy-6-oxo-N-phenyl-5-pyrimidinecarboxamide and 3,4-dihydro-6-hydroxy-2-methoxy-4-oxo-N-phenyl-5-pyrimidinecarboxamide. The invention will be described in greater detail in connection with the following specific examples illustrating the preparation and testing of these compounds:

EXAMPLE 1

3,4Dihydro-4-hydroxy-6-oxo-N-phenyl-5-pyrimidinecarboxamide

To concentrated aqueous ammonium hydroxide (400 ml) and water (400 ml) was added 1,2,3,4-tetrahydro-6-hydroxy-4-oxo-N-phenyl-2-thioxo-5-pyrimidinecarboxamide (13.2 g) (prepared as described in Example 1 of the aforesaid copending application Ser. No. 699,776). The pyrimidine dissolved. To this solution was added a slurry of Raney Nickel in water (50 g). The suspension was gently refluxed with stirring for four hours. It was cooled and the solids, which consisted of product and inorganics, were treated with dilute hydrochloric acid, the mixture filtered and the solids extracted with 2-Normal sodium hydroxide solution and filtered. The filtrate was then acidified with dilute hydrochloric acid, the resulting precipitate redissolved in aqueous ammonium hydroxide, purified with activated charcoal and celite, and reprecipitated with dilute acid. The solid was collected, washed with water and dried. Yield 5.8 g, melting point 200°–208°. Mass spectrum 231, calculated 231; Nuclear Magnetic Resonance (DMSO), 6.8–7.7 δ (aromatic peaks); 8.28 δ (2-hydrogen atom); 11.8 δ (exchangeable protons).

EXAMPLE 2

3,4-Dihydro-6-hydroxy-2-methoxy-4-oxo-N-phenyl-5-pyrimidinecarboxamide

To a solution of 4,6-dihydroxy-2-methoxypyrimidine (6 g) in dry dimethyl sulfoxide was added triethylamine (5.9 ml). The solution was brought to 60° and phenyl isocyanate (5 g) was added; the solution was maintained at 80°-90° for two hours, cooled and water added slowly to cause precipitation.

The product was obtained as an off-white solid, melting point 164°-168°. Analysis; calculated for $C_{12}H_{11}N_3O_4$, C, 55.17%; H 4.21%; N 16.09%; found, C, 54.84%; H, 4.17%; N, 15.85%. Mass spectrum, calculated, 261, found 261. Nuclear magnetic resonance spectrum (DMSO); 3.93 δ (singlet integral 3); 7.1-7.7 δ (broad complex singlet, integral 6); 14.2 δ (broad singlet, integral 1).

Comparison of the Antitumor Activities of the Compounds of Examples 1 and 2 with other 5-Pyrimidinecarboxamides in the Regression of i p.-Implanted Lymphoid Leukemia L1210

Samples of the test compounds of Examples 1 and 2 and other 5-pyrimidinecarboxamides of similar structures were tested in vivo in accordance with National Cancer Institute test protocol 3LE31 (NCI Protocol 1.100, Cancer Chemotherapy Reports Part 3, Vol. 3, No. 2, September 1972) to determine the effects of the compounds on i.p.-implanted L1210 leukemia (J. Nat'l. Cancer Inst. 13(5):1328, 1953). Each test involved implantation of the leukemia cells in six DBA/2 mice, one sex per experiment, the male mice weighing a minimum of 18 grams and the female mice weighing a minimum of 17 grams, and all of the test animals being within a three gram weight range. The test compounds were aministered by i.p. injections, in 0.1 ml. doses of diluted ascitic fluid ($10^5$ cells per dose), commencing one day ater the tumor implant and continuing daily for nine days.

The test animals were weighed and survivors recorded on a regular basis during a thirty day test period. The ratio of survival time for the treated and control animals (T/C) was determined as a percentage.

The tests were carried out at varying dosage levels depending upon the results obtained with each test compound. It has been statistically determined in the 3LE31 test system that an initial T/C value at least equal to 125% is necessary to demonstrate activity, while a reproducible T/C equal to or greater than 125% warrants further study. A reproducible T/C of 150% or higher is considered significant activity.

Comparative Activities Against i.p.-Implanted L 1210 Leukemia Test Compounds:

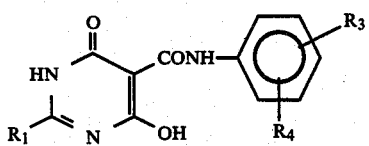

| Compound | $R_1$ | $R_3$ | $R_4$ | Dose (mg/kg) | T/C % | T/C % (Repeat) |
|---|---|---|---|---|---|---|
| Example 1 | H | H | H | 200 | 110 | 116 |

Comparative Activities Against i.p.-Implanted L 1210 Leukemia Test Compounds:

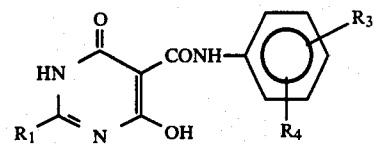

| Compound | $R_1$ | $R_3$ | $R_4$ | Dose (mg/kg) | T/C % | T/C % (Repeat) |
|---|---|---|---|---|---|---|
| 1 | | | | 100 | 186 | 185 |
| | | | | 50 | 122 | 131 |
| | | | | 25 | 116 | 107 |
| Example 2 | —OCH$_3$ | H | H | 200 | 144 | 155 |
| | | | | 100 | 110 | 118 |
| | | | | 50 | 106 | 109 |
| | | | | 25 | 102 | 108 |
| | | | | 12.5 | | 101 |
| Control A | —CH$_3$ | H | H | 200 | 109 | |
| | | | | 100 | 102 | |
| | | | | 50 | 98 | |
| | | | | 25 | 105 | |
| Control B | —NH$_2$ | H | H | 200 | 96 | |
| | | | | 100 | 103 | |
| | | | | 50 | 98 | |
| | | | | 25 | 103 | |
| Control C | —NHCH$_3$ | H | H | 200 | 97 | |
| | | | | 100 | 101 | |
| | | | | 50 | 94 | |
| | | | | 25 | 94 | |
| Control D | —NHC$_{12}$H$_{25}$ | H | H | 200 | 95 | |
| | | | | 100 | 95 | |
| | | | | 50 | 101 | |
| | | | | 25 | 98 | |
| Control E | —NHCOPh | H | H | 200 | 95 | |
| | | | | 100 | 95 | |
| | | | | 50 | 103 | |
| | | | | 25 | 104 | |
| Control F | —NHNHPh | 2-CH$_3$ | 5-CH$_3$ | 200 | 95 | |
| | | | | 100 | 98 | |
| | | | | 50 | 98 | |
| | | | | 25 | 100 | |
| Control G | —N(CH$_3$)$_2$ | H | H | 200 | 101 | |
| | | | | 100 | 101 | |
| | | | | 50 | 98 | |
| | | | | 25 | 98 | |
| Control H | —SCH$_3$ | H | H | 200 | 91 | |
| | | | | 100 | 91 | |
| | | | | 50 | 86 | |
| | | | | 25 | — | |
| Control I | —SCH$_3$ | 2-CH$_3$ | 5-CH$_3$ | 200 | 102 | |
| | | | | 100 | 94 | |
| | | | | 50 | 104 | |
| | | | | 25 | 104 | |
| Control J | —SCH$_3$ | 3-OCH$_3$ | H | 200 | — | |
| | | | | 100 | 93 | |
| | | | | 50 | 93 | |
| | | | | 25 | 97 | |
| Control K | —SCH$_3$ | 2-CF$_3$ | H | 200 | 99 | |
| | | | | 100 | 99 | |
| | | | | 50 | 118 | |
| | | | | 25 | 101 | |
| Control L | —SCH$_3$ | 2-Cl | H | 200 | 101 | |
| | | | | 100 | 94 | |
| | | | | 50 | 95 | |
| | | | | 25 | 101 | |
| Control M | —SCH$_3$ | 2-F | H | 200 | 92 | |
| | | | | 100 | 93 | |
| | | | | 50 | 96 | |
| | | | | 25 | 94 | |
| Control N | —SCH$_3$ | 3-F | H | 200 | 104 | |
| | | | | 100 | 104 | |
| | | | | 50 | 95 | |
| | | | | 25 | 96 | |
| Control O | —SCH$_3$ | 4-F | H | 200 | 98 | |
| | | | | 100 | 101 | |
| | | | | 50 | 94 | |

-continued

Comparative Activities Against i.p.-Implanted L 1210 Leukemia
Test Compounds:

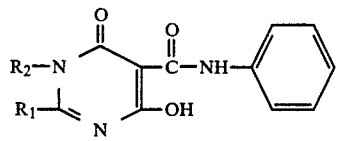

| Compound | $R_1$ | $R_3$ | $R_4$ | Dose (mg/kg) | T/C % | T/C % (Repeat) |
|---|---|---|---|---|---|---|
| Control P | —SCH₃ | 2-F | 4-F | 25 | 98 | |
| | | | | 200 | 93 | |
| | | | | 100 | 90 | |
| | | | | 50 | 91 | |
| | | | | 25 | 97 | |

A further control compound, 3-4-dihydro-4-hydroxy-6-oxo-N-phenyl-5-pyrimidinethiocarboxamide—Control P, was tested by the 3LE31 protocol as described above. The compound, the thio-analog of the compound of Example 1, was found inactive in vivo. It exhibited the following activity:

| Dose (mg./kg.) | T/C % |
|---|---|
| 200 | 98 |
| 100 | 96 |
| 50 | 92 |
| 25 | 96 |

From the preceding, it will be seen that, in accordance with the present invention, a class of novel 5-pyrimidinecarboxamides is provided, the members of which exhibit substantial cytotoxic activity and induce regression and/or inhibit growth of leukemia and various malignant tumors in mammals. It will be apparent that various changes may be made in the method of preparation and use, as well as in the particular substitution, of the therapeutically active compounds of the invention. Accordingly, the preceding disclosure should be construed as illustrative only, and the scope of the invention should be interpreted in accordance with the claims appended hereto.

We claim:

1. A method for inducing the regression of leukemia in a host, which comprises treating the host with an effective amount of a compound of the formula:

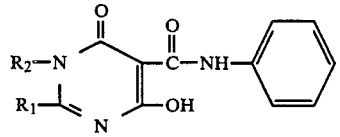

wherein $R_1$ is an alkoxy group having from one to four carbon atoms:

$R_2$ is hydrogen or a carbohydrate residue selected from the group consisting of furanosyl, pyranosyl, glucopyranosyl or galactopyranosyl groups, their deoxy derivatives, and hydroxyalkoxyalkyl and polyhydroxyalkyl groups having from 2-12 carbon atoms in each of the alkoxy and alkyl moieties thereof; and the pharmaceutically acceptable addition salts thereof.

2. The method of claim 1, wherein the active compound is 3,4-dihydro-6-hydroxy-2-methoxy-4-oxo-N-phenyl-5-pyrimidinecarboxamide.

3. A 5-pyrimidinecarboxamide of the formula:

wherein $R_1$ is an alkoxy group having from one to four carbon atoms:

$R_2$ is hydrogen or a carbohydrate residue selected from the group consisting of furanosyl, pyranosyl, glucopyranosyl or galactopyranosyl groups, their deoxy derivatives, and hydroxyalkoxyalkyl and polyhydroxyalkyl groups having from 2-12 carbon atoms in each of the alkoxy and alkyl moieties thereof; and the pharmaceutically acceptable addition salts thereof.

4. The 5-pyrimidinecarboxamide of claim 6, viz., 3,4-dihydro-6-hydroxy-2-methoxy-4-oxo-N-phenyl-5-pyrimidinecarboxamide.

5. A pharmaceutical composition for inducing regression of leukemia, which comprises an effective amount of the compound of claim 6, in admixture with a pharmaceutically acceptable, substantially nontoxic carrier or excipient.

6. A pharmaceutical composition for inducing regression of leukemia, which comprises an effective amount of the compound of claim 10, in admixture with a pharmaceutically acceptable, substantially nontoxic carrier or excipient.

* * * * *